(12) United States Patent
Huang et al.

(10) Patent No.: US 11,020,094 B2
(45) Date of Patent: Jun. 1, 2021

(54) METHOD AND SYSTEM FOR PROCESSING ULTRASONIC IMAGING DATA

(71) Applicant: KONINKLIJKE PHILIPS N.V., Eindhoven (NL)

(72) Inventors: Kai Huang, Eindhoven (NL); Ying Wu, Eindhoven (NL); Yinhui Deng, Eindhoven (NL); Xiaomin Li, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 298 days.

(21) Appl. No.: 14/415,252

(22) PCT Filed: Jul. 1, 2013

(86) PCT No.: PCT/IB2013/055382
§ 371 (c)(1),
(2) Date: Jan. 16, 2015

(87) PCT Pub. No.: WO2014/013366
PCT Pub. Date: Jan. 23, 2014

(65) Prior Publication Data
US 2015/0190120 A1    Jul. 9, 2015

(30) Foreign Application Priority Data

Jul. 18, 2012 (WO) ............... PCT/CN2012/078816

(51) Int. Cl.
*A61B 8/08* (2006.01)
*A61B 8/00* (2006.01)

(52) U.S. Cl.
CPC ............ *A61B 8/5223* (2013.01); *A61B 8/085* (2013.01); *A61B 8/469* (2013.01); *A61B 8/485* (2013.01)

(58) Field of Classification Search
CPC ....... A61B 8/5223; A61B 8/085; A61B 8/485; A61B 8/469; A61B 6/507; A61B 6/5217;
(Continued)

(56) References Cited

U.S. PATENT DOCUMENTS 5,551,434 A    9/1996 Iinuma
6,306,089 B1*  10/2001 Coleman ............. G01S 7/52023
                                                            128/916
(Continued)

FOREIGN PATENT DOCUMENTS

CN    101599174 A    12/2009
EP    1582150 A1     5/2005
(Continued)

OTHER PUBLICATIONS

Cosgrove et al. 2012 Eur.Radiol. 22:1023-1032. ePub.Date Dec. 31, 2011.*
(Continued)

*Primary Examiner* — Keith M Raymond
*Assistant Examiner* — Patrick M Mehl

(57) ABSTRACT

The present invention provides a method and a system for processing ultrasonic data. The method comprises: obtaining (210) a B-mode ultrasonic image; setting (220) a first ROI on the ultrasonic image according to a first input received from a user; measuring (230) elasticity-related data for the first ROI by using a shear wave ultrasonic imaging technique; generating (240) a second ROI on the ultrasonic image on the basis of the first ROI; and extracting image features for the second ROI from the ultrasonic image.

19 Claims, 1 Drawing Sheet

(58) Field of Classification Search
CPC ......... A61B 6/486; A61B 6/503; A61B 6/583; A61B 6/12; A61B 6/464; A61B 6/5235; A61B 6/4441; G06T 5/008; G06T 5/50; G06T 7/0012; G06T 2207/30104; G06T 2207/10116
See application file for complete search history.

(56) References Cited

U.S. PATENT DOCUMENTS

| | | | |
|---|---|---|---|
| 6,508,768 | B1 | 1/2003 | Hall et al. |
| 7,090,640 | B2* | 8/2006 | Barth ............... A61B 8/0858 382/128 |
| 7,397,937 | B2* | 7/2008 | Schneider .......... G16H 15/00 382/130 |
| 8,019,133 | B2* | 9/2011 | Knoplioch .......... G06K 9/342 345/419 |
| 2005/0283076 | A1* | 12/2005 | Hangiandreou ...... A61B 8/485 600/443 |
| 2009/0088623 | A1* | 4/2009 | Vortman ............. A61B 8/5276 600/411 |
| 2010/0016718 | A1 | 1/2010 | Fan et al. |
| 2010/0286520 | A1 | 11/2010 | Hazard et al. |
| 2010/0317971 | A1 | 12/2010 | Fan et al. |
| 2011/0130660 | A1* | 6/2011 | Cloutier ............ A61B 5/02007 600/438 |
| 2011/0152687 | A1* | 6/2011 | Iimura ................ A61B 8/08 600/443 |
| 2011/0245673 | A1* | 10/2011 | Kamiyama ........... A61B 8/08 600/443 |
| 2011/0306884 | A1 | 12/2011 | Tanigawa et al. |
| 2012/0170850 | A1* | 7/2012 | Lam .................... G06T 7/337 382/195 |

FOREIGN PATENT DOCUMENTS

| | | |
|---|---|---|
| JP | 2007075184 A | 3/2007 |
| JP | 2011045587 A | 10/2011 |
| JP | 2012100841 A | 5/2012 |
| RU | 2179313 C2 | 2/2002 |
| WO | 2011064688 A1 | 6/2011 |
| WO | 2012035472 A1 | 3/2012 |

OTHER PUBLICATIONS

Lankton et al. 2008 IEEE Trans. Image Processing 17:2029-2039.*
Fahey et al. 2008 Phys. Med. Biol. 53:279-293.*
Bolondi et al. 2001 Gut 48:251 -259.*
Hafizah et al. 2011 Automatic Region of Interest Generation for Kidney Ultrasound Images in Recent Researches in Applied Informatics and Remote Sensing, Proc. 11th WSEAS Int. Conf. Applied Computer Science ACS'11, Penang, Malaysia, pp. 70-75 (Year: 2011).*
Boctor et al. 2006 LNCS 4191 chapter 4 in section Image Guided Intervention p. 405-412 (Year: 2006).*
Yap et al. 2008 FSKD 2005, LNAI 3614 p. 1079-1088 (Year: 2008).*
Shan et al. 2012 Ultrasound in Med. & Biol. 38:262-275 (Year: 2012).*
Athanasiou et al. 2010 Radiology 256:297-303 (Year: 2010).*
"Ultrasonic Multifeature Tissue Characterization for Prostate Diagnostics" Scheipers et al, Ultrasound in Med. and Biol. vol. 29, No. 8, p. 1137-1149 (2003).
"Elastography: Ultrasonic Estimation and Imaging of the Elastic Properties of Tissues" Ophir et al, Proc. Instn. Mech. Engrs. vol. 213 Part H (1999).
Localizing Region-Based Active Contours, Lankton et al, IEEE Transactions on Image Processing vol. 17, No. 11 Nov. 2008.

* cited by examiner

METHOD AND SYSTEM FOR PROCESSING ULTRASONIC IMAGING DATA

This application is the U.S. National Phase application under 35 U.S.C. § 371 of International Application No. PCT/IB2013/055382, filed on Jul. 1, 2013, which claims the benefit of International Application No. PCT/CN2012/078816 filed on Jul. 18, 2012. These applications are hereby incorporated by reference herein.

FIELD OF THE INVENTION

The invention relates to an ultrasound-based imaging method and system, and particularly to the processing of ultrasonic imaging data.

BACKGROUND OF THE INVENTION

Ultrasonic imaging has been widely accepted as an easy-to-use, inexpensive imaging modality to diagnose malignant cancers such as breast, liver, prostate cancers, etc. However, clinical doctors still have less confidence in the ability of using ultrasound to differentiate benign and malignant lesions because ultrasound has relatively poor image quality and operator-dependence compared to other imaging modalities such as computed tomography (CT) and Magnetic Resonance Imaging (MRI).

In recent years, a computer aided diagnosis (CAD) system, which is also referred to as computer decision support (CSD) system, has been developed to help clinical doctors to detect or diagnose lesions.

The current ultrasound-based CAD system relies on B-mode ultrasonic images. For example, anatomical information extracted from the B-mode ultrasonic images may be used for the computer aided diagnosis in a CAD system. In order to obtain the anatomical information of the relevant tissues, a user needs to manually set a region of interest (ROI) on the B-mode ultrasonic images. Then the anatomical information for the ROI may be extracted from the B-mode ultrasonic images and may be used for the computer aided diagnosis in the CDS system.

However, the anatomical information extracted from the B-mode ultrasonic images becomes insufficient for the CDS system. It is desirable to improve the performance of computer aided diagnosis by using for example another category of information in the ultrasound-based CAD system.

Ultrasonic elastography, for example a shear-wave ultrasonic imaging technique, is another ultrasonic imaging mode which can provide elasticity-related data (i.e., stiffness) of tissues. For example, Philips has developed the shear-wave ultrasonic elastography point quantification (elastoPQ) technique, which can provide quantitative mechanical information (i.e., stiffness) of tissues. In order to obtain the elasticity-related information of the relevant tissues, a user needs to manually set a ROI on the B-mode ultrasonic image to outline the relevant area, and then the shear-wave ultrasonic imaging procedure may be performed to obtain the elasticity-related information for the relevant area.

Our research results indicate that the combination of B-mode imaging technique and elastoPQ technique can improve the sensitivity and specificity of lesion detection and differentiation in the ultrasound-based CAD system. However, in order to obtain the anatomical information and the elasticity-related information, the user, such as the clinical doctor, needs to set the ROI for obtaining the anatomical information and the ROI for obtaining the elasticity-related information separately in the above-mentioned procedures to obtain the two kinds of information. In this way, the user's operation and experience are paramount to ensure that the two ROIs target the same relevant tissue area.

Therefore, it is desirable to provide a more efficient and reliable method and system for providing the two kinds of information to the ultrasound-based CAD system.

SUMMARY OF THE INVENTION

For the sake of the above mentioned purpose, the present invention provides a method and system for facilitating the ultrasound-based computer aided diagnosis. The present invention can simplify the operation of the user for setting the two ROIs and make sure that the two ROIs target the same relevant tissue area.

According to an aspect of the present invention, a method of processing ultrasonic data is provided, the method comprising: obtaining a B-mode ultrasonic image; setting a first ROI on the ultrasonic image according to a first input received from a user; measuring elasticity related data for the first ROI by using a shear wave ultrasonic imaging technique; generating a second ROI on the ultrasonic image on the basis of the first ROI; and extracting image features for the second ROI from the ultrasonic image.

In this method, through using the measurement box, i.e., the first ROI, for one mode of ultrasonic imaging, i.e., shear wave ultrasonic imaging (elastoPQ as an example) as the basis for generating the second ROI for the processing of another mode of ultrasonic images, i.e., B-mode ultrasonic images, the user only needs to set the ROI once and the second ROI is automatically generated based on the ROI set by the user. In this way, the user operation is simplified and the first and second ROIs are sure to target the same or a corresponding relevant tissue area with respect to the two kinds of information, i.e., the elasticity-related information and the anatomical information.

According to an embodiment of the present invention, the method further comprises receiving a second input from the user.

In this embodiment, the step of generating the second ROI comprises:

if the second input indicates a lesion application, generating, on the basis of the first ROI, a contour of the lesion in the ultrasonic image as the second ROI;

if the second input indicates a non-lesion application, generating the second region of interest around the first ROI as the second ROI according to a predetermined shape.

In this embodiment, through generating the second ROI in different ways according to the related clinical applications, the second ROI may be set in a more accurate manner.

According to an embodiment of the present invention, the step of generating a predetermined shape around the first ROI as the second ROI comprises: using the first ROI as the second ROI; or generating the second region of interest by expanding from the first ROI by a predetermined factor.

In this embodiment, for the non-lesion application, the simplest way to generate the second ROI is to use the first ROI as the second ROI. In this way the processing complexity may be reduced.

According to an embodiment of the present invention, the method further comprises receiving a third input from the user, and adjusting the second ROI according to the third input received from the user.

In this embodiment, the user is allowed to adjust the generated second ROI manually.

According to another aspect of the present invention, a system for processing ultrasonic data is provided, the system comprising: an ultrasonic probe; a B-mode imaging unit for obtaining a B-mode ultrasonic image from ultrasonic radio-frequency data collected by the ultrasonic probe; a user interface for receiving a first input of a user and setting a first ROI on the ultrasonic image according to the first user input; an elasticity measuring unit for measuring elasticity-related data for the first ROI by using a shear wave ultrasonic imaging technique; and an image processing unit for generating a second ROI on the ultrasonic image on the basis of the first ROI and extracting image features for the second ROI from the ultrasonic image.

In this aspect, the present invention provides a system in which the elasticity-related information and the anatomical information may be efficiently obtained and reliably relate to the same or a corresponding relevant tissue area. And in this system, the user only needs to set the first ROI once and the second ROI is automatically generated by an image processing unit, based on the first ROI; in this way the user operation is simplified and two ROIs are sure to target the same or a corresponding relevant tissue area.

According to an embodiment of the present invention, the user interface is adapted for receiving a second user input. And in this embodiment, the image processing unit may be adapted for:

if the second input indicates a lesion application, generating, on the basis of the first ROI, a contour of the lesion in the ultrasonic image as the second ROI;

if the second input indicates a non-lesion application, generating the second region of interest around the first ROI according to a predetermined shape.

And in this embodiment, the image processing unit may be further adapted for: using the first ROI as the second ROI, or for generating the second region of interest by expanding from the first ROI by a predetermined factor.

According to an embodiment of the present invention, the user interface may be adapted for receiving a third input from the user and adjusting the second ROI according to the third input received from the user.

According to another aspect of the present invention, a computer program product is provided comprising machine executable instruction codes which, when executed on a machine, cause the machine to perform the above mentioned methods for processing ultrasonic data.

According to another aspect of the present invention, an ultrasonic imaging apparatus is provided which comprises an image processor for processing ultrasonic data, the image processor being configured to perform the above mentioned methods.

Other objects and advantages of the present invention will become more apparent from and will be easily understood with reference to the description made in combination with the accompanying drawings.

DESCRIPTION OF THE DRAWINGS

The present invention will be described and explained hereinafter in more detail by means of embodiments and with reference to the drawings, in which.

The same reference signs in the figures indicate similar or corresponding features and/or functionalities.

DETAILED DESCRIPTION

Embodiments of the present invention will be described hereinafter in more detail with reference to the drawings.

Figure 1:
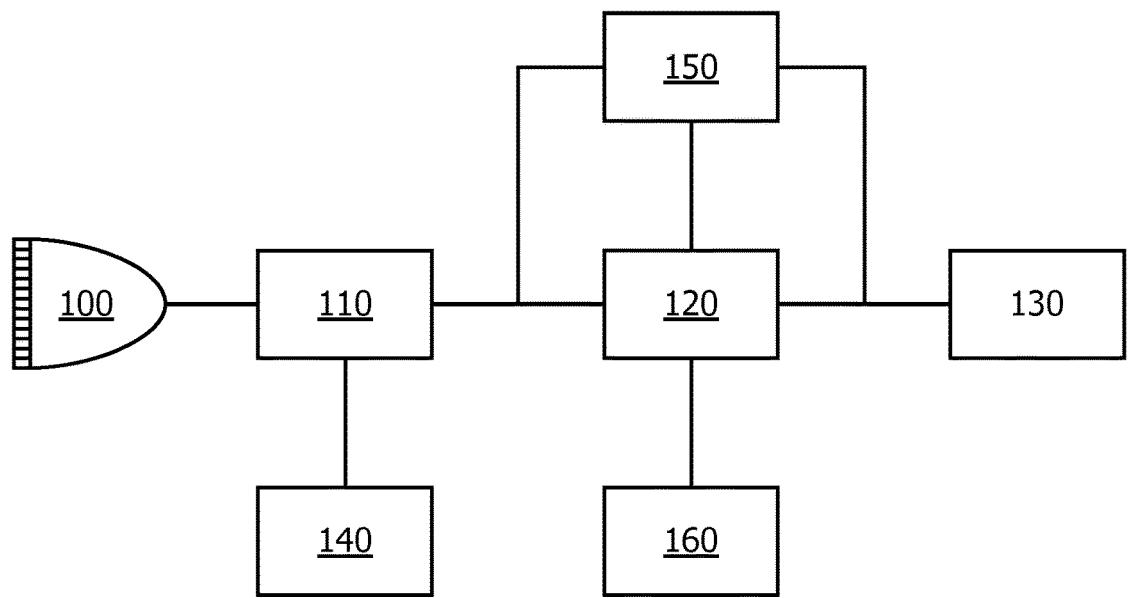
FIG. 1 is a block diagram which illustrates an ultrasonic diagnostic imaging system constructed in accordance with an embodiment of the present invention.

Referring to FIG. 1, an ultrasonic system constructed in accordance with an embodiment of the present invention is shown in the block diagram.

An ultrasonic probe 100 has a transducer array of transducer elements for transmitting and receiving ultrasonic signals. The transducer array can be a one-dimensional or a two-dimensional array of transducer elements. Either type of transducer array can scan a two-dimensional (2D) plane and the two-dimensional array can be used to scan a volumetric region in front of the array.

The ultrasonic probe 100 is coupled to a B-mode imaging unit 110. The B-mode imaging unit 110 may obtain B-mode ultrasonic images from the ultrasonic radio-frequency data collected by the ultrasonic probe 100. The obtained B-mode ultrasonic images may be displayed on the display 150 which is coupled to the B-mode imaging unit 110. And the obtained B-mode ultrasonic images may also be further processed in the image processing unit 120 which is coupled to the B-mode imaging unit 110.

While viewing the displayed B-mode ultrasonic image, a user such as a clinical doctor or a radiologist may set a first ROI on the B-mode ultrasonic image via the user interface 130, which is coupled to the image processing unit 120 and/or to the elasticity measuring unit 140 (not shown in the FIG. 1). In other words, the user interface may receive a user input and set a first ROI on the ultrasonic image according to the user input. The first ROI set via the user interface may be used by the elasticity measuring unit 140 to perform the measurement of elasticity-related data for the first ROI. The measurement of elasticity-related data may be performed by using a shear wave ultrasonic imaging technique. Such a shear wave ultrasonic imaging technique is described in Philips's patent application WO2011/064688, which is referred to in this application. And the measurement of elasticity-related data may be performed by using the shear-wave ultrasonic elastography point quantification (elastoPQ) technique developed by Phillips. Then the measured elasticity-related data may be provided to the CDS system 160 for the purpose of computer aided diagnosis.

The image processing unit 120 may generate a second ROI on the ultrasonic image on the basis of the first ROI set via the user interface. And the image processing unit 120 may perform further processing of the B-mode ultrasonic images with respect to the second ROI. According to an embodiment, the image processing unit 120 may extract image features for the second ROI from the B-mode ultrasonic images. The extracted image features may present the anatomical information of the relevant tissue area outlined by the second ROI; for example, the image features extracted for the second ROI may be morphological features, texture features, margin features and so on, which may be provided in the CDS system 160 for the purpose of computer aided diagnosis.

In the above embodiment, the extraction of image features is performed by the image processing unit 120 outside the CDS system 160. However, in a variation of the embodiment, the functional unit for extracting image features may be implemented in the CDS system 160. In this variation of embodiment, the image processing unit 120 may provide the B-mode ultrasonic images having the second ROI thereon to the CDS system 160, and a feature extracting unit of the CDS system may extract the image features for the second ROI from the B-mode ultrasonic images.

In the above embodiment, the measured elasticity-related data and the extracted image features are provided to the CDS system 160 for the computer aided diagnosis. However, it should be understood that the CDS system should not be considered as a necessary component for the implementation of the system of the present invention. For example, the measured elasticity-related data and the extracted image features may be displayed to the user just for facilitating the user's diagnosis. And in another example, the measured elasticity-related data and the extracted image features may be simultaneously displayed to the user and provided to the CDS system.

In an embodiment, the image processing unit 120 may generate the second ROI in different manners according to different clinical applications. In this embodiment, the user may specify, via the user interface 130, what kind of clinical application the present diagnosis relates to; in other words, the user interface may present a prompt to the user to select the type of clinical application and receive a user input, which is referred to as a second user input hereafter.

If the second input indicates that the application is a lesion application, for example, to differentiate malignant lesion from cirrhosis nodule, then the image processing unit 120 may generate a contour of the lesion in the ultrasonic image on the basis of the first ROI for measuring elasticity information and use the contour as the second ROI for extracting anatomical information. In order to accurately measure the elasticity information of the relevant tissue area, such as a lesion, the user typically needs to set the first ROI within the lesion area. Therefore, the contour of the lesion area may be generated by a segmentation technique based on the first ROI. For example, the segmentation technique may use the first ROI as the initial contour and achieve the contour of the lesion by expanding the initial contour to the real contour. It should be understood that in order to achieve the contour of the lesion, it is not compulsory to set the first ROI perfectly within the lesion area. The contour of the lesion may be achieved as long as the first ROI roughly overlaps the lesion area. An exemplary segmentation technique for detecting a contour of a subject on the basis of an initially set contour which roughly covers the subject is provided in "Localizing Region-Based Active Contours", Shawn Lankton, et al, IEEE TRANSACTIONS ON IMAGE PROCESSING, VOL. 17, NO. 11, NOVEMBER 2008, which is referred to in this application. And the exemplary segmentation technique may be used by the image processing unit to generate the contour of the lesion on the basis of the first ROI. In an example, after the contour is generated as the second ROI, it may be desirable for the user to manually adjust the second ROI, and in some cases manual adjustment by the user might be needed. Therefore, in this example, the user may be allowed to adjust the second ROI via the user interface; in other words, the user interface may receive further input from the user and adjust the second ROI according to the user's input.

If the second input indicates that the application is a non-lesion application, for example, to classify liver cirrhosis, distinguish fatty liver from normal liver, then the image processing unit 120 may generate the second ROI in a different way. For example, the image processing unit 120 may generate the second ROI around the first ROI according to a predetermined shape. In an example, the image processing unit may use the first ROI as the second ROI. In another example, the image processing unit may expand the first ROI by a predetermined factor and use the expanded shape from the first ROI as the second ROI. The factor may be an experimental value and may be set beforehand. In an example, the user is allowed to adjust the factor via the user interface in order to adjust the expanded shape; in other words, the user interface may receive further user input and adjust the second ROI according to the user input.

It is described in the above embodiment that different ways are used to generate the second ROI according to different clinical applications. However, the present invention is not limited to a specific way of generating the second ROI. For example, any way of generating the second ROI as described above may be used in any clinical application. And other ways to generate the second ROI based on the first ROI are also applicable in the present invention.

Figure 2:
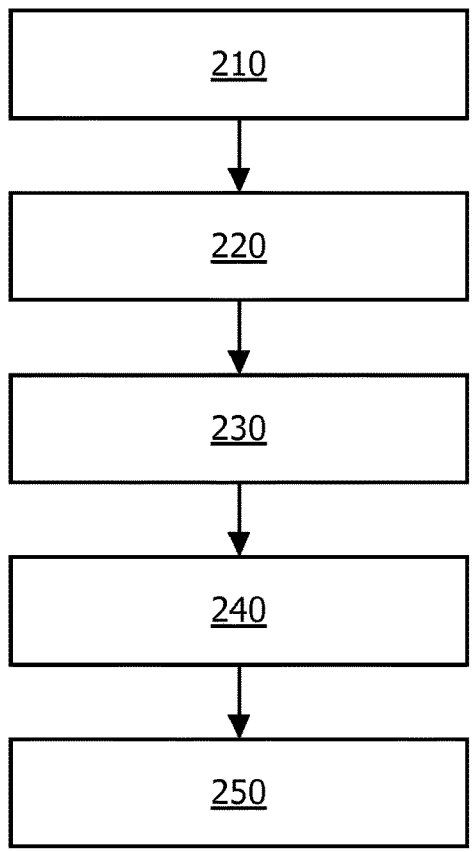
FIG. 2 is a flowchart of a method for the combined use of shear-wave ultrasonic imaging technique and B-mode ultrasonic imaging technique in accordance with an embodiment of the present invention.

Referring to FIG. 2, a method for combined use of a shear-wave ultrasonic imaging technique and a B-mode ultrasonic imaging technique is shown in the block diagram.

At step 210, a B-mode ultrasonic image may be obtained.

At step 220, a first ROI may be set on the ultrasonic image according to a first input received from a user.

At step 230, elasticity-related data for the first ROI may be measured by using a shear wave ultrasonic imaging technique.

At step 240, a second ROI may be generated on the ultrasonic image on the basis of the first ROI.

At step 250, image features may be extracted for the second ROI from the ultrasonic image.

Although the steps of the method are shown as sequential steps, it should be understood that the present invention is not limited to the specific sequence of the steps. For example, step 230 may be performed in parallel with steps 240 and 250.

According to an embodiment of the present invention, the second ROI may be generated in different ways according to different clinical applications. In this embodiment, before generating the second ROI at step 240, the method may further comprise receiving a second input from the user. If the second input indicates a lesion application, then at step 240, a contour of the lesion in the ultrasonic image may be generated on the basis of the first ROI and may be used as the second ROI. If the second input indicates a non-lesion application, the second ROI may be generated in a different way at step 240; for example, the second ROI around the first ROI may be generated according to a predetermined shape. In an example, the first ROI may be used as the second ROI. In another example, the first ROI may be expanded by a predetermined factor and the shape expanded from the first ROI may be used as the second ROI. The factor may be an experimental value and may be set beforehand. And, in an example, a third input may be received from the user, and the second ROI may be adjusted according to the third input received from the user.

It should be understood that some units as shown in FIG. 1 may be implemented in a processor, or may be implemented in several hardware components; for example, the B-mode ultrasonic imaging unit 110, the image processing unit 120 and the shear wave ultrasonic imaging unit 140 may be implemented respectively in a dedicated processing unit such as a Digital Signal Processor (DSP) or an Application Specific Integrated Circuit (ASIC) or the like designed specifically for implementing their functions.

It should be understood that method 200 as shown in FIG. 2 may be implemented in software as a computer program product, the described process may be stored on or transmitted as program instructions or codes on a computer-readable medium. And a processor such as a general purpose processor or a specific purpose processor may be used, when executing the program instructions, to perform the method as described above. Computer-readable media include any medium that facilitates transfer of a computer program from one place to another and that can be accessed by a computer. By way of example, the computer-readable media may include RAM, ROM, EEPROM, CD-ROM or other optical disk storage, magnetic disk storage or other magnetic storage devices, or any other medium that can be used to carry or store desired program codes in the form of instructions or data structures and that can be accessed by a computer.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A method of rendering ultrasonic data, comprising:
controlling, with an imaging unit, an ultrasonic probe in communication with the imaging unit to generate a B-mode ultrasonic image;
receiving, at a user interface in communication with an image processing unit, a first input from a user;
setting a boundary of a first region of interest on the B-mode ultrasonic image based on the first input;
controlling, with an elasticity measuring unit, the ultrasonic probe to generate elasticity-related data corresponding to the first region of interest;
initiating different computer aided diagnosis operations of the imaging processing unit for different clinical applications, wherein the initiating includes:
presenting, via the user interface, a prompt to select the clinical application type from among a plurality including a lesion application and a non-lesion application;
receiving, from the user at the user interface, a second input indicating a selection of the clinical application type;
automatically generating, by the image processing unit, a second region of interest for the B-mode ultrasonic image based on the first region of interest and the selection of the clinical application type, wherein the second region of interest is different than the first region of interest, wherein the first region of interest and the second region of interest comprises an overlapping portion, wherein generating the second region of interest comprises:
if the selection of the clinical application type indicates the lesion application, generating, based on an image content of the first region of interest, a contour of a lesion within the first region of interest in the B-mode ultrasonic image as the second region of interest; and
if the selection of the clinical application type indicates the non-lesion application, generating the second region of interest by expanding the first region of interest according to at least one of a predetermined shape or a predetermined factor;
applying the second region of interest to the B-mode ultrasonic image;
extracting, by the image processing unit, image features corresponding to the second region of interest in the B-mode ultrasonic image; and
simultaneously outputting, to a display, the elasticity-related data corresponding to the first region of interest and the extracted image features corresponding to the second region of interest, wherein the elasticity-related data and the extracted images features comprise anatomical information of the overlapping portion.

2. The method of claim 1, wherein, if the selection of the clinical application type indicates the lesion application, the contour is generated by identifying contour points in the first region of interest and in a predefined area around the first region of interest.

3. The method of claim 1, wherein generating the second region of interest around the first region of interest according to the at least one of the predetermined shape or the predetermined factor comprises:
using the first region of interest as the second region of interest.

4. The method of claim 1, further comprising: receiving a third input from the user to adjust the second region of interest; and
adjusting an outline of the second region of interest from a first outline to a second outline according to the third input received from the user,
wherein the extracted image features correspond to image features within the second outline of the second region of interest in the B-mode ultrasonic image.

5. A computer system comprising instruction codes for performing the method of claim 1.

6. An ultrasonic imaging apparatus comprising:
an image processing system configured to perform the method of claim 1.

7. The method of claim 1, wherein the image features comprise a morphological feature, a texture feature, or a margin feature.

8. The method of claim 1, further comprising:
performing a segmentation technique based on the first region of interest to generate the second region of interest.

9. The method of claim 1, wherein automatically generating the second region of interest comprises generating the second region of interest without receiving a user input to set a boundary of the second region of interest.

10. The method of claim 1, further comprising transmitting the elasticity-related data corresponding to the first region of interest and the extracted image features to a computer decision support system (CDS).

11. A system for processing ultrasonic data, comprising:
an ultrasonic probe;
an imaging unit configured to control the ultrasonic probe to generate a B-mode ultrasonic image;
a user interface configured to:
receive a first input of a user and to set a boundary of a first region of interest on the B-mode ultrasonic image based on the first input;
present a prompt to select a clinical application type from among a plurality including a lesion application and a non-lesion application; and
receive a second input indicating a selection of the clinical application type;

an elasticity measuring unit configured to control the ultrasonic probe to generate elasticity-related data corresponding to the first region of interest; and an image processing unit in communication with the user interface and configured to initiate different computer aided diagnosis operations for different clinical applications, wherein, to initiate the different computer aided diagnosis operations, the imaging processing unit is configured to:

automatically generate a second region of interest for the B-mode ultrasonic image based on the first region of interest and the selection of the clinical application type, wherein the second region of interest is different than the first region of interest, wherein the first region of interest and the second region of interest comprises an overlapping portion, wherein generating the second region of interest comprises:

generating, based on an image content of the first region of interest, a contour of a lesion within the first region of interest in the B-mode ultrasonic image as the second region of interest, when the selection of the clinical application type indicates the lesion application; and generating the second region of interest by expanding the first region of interest according to at least one of a predetermined factor or a predetermined shape, when the selection of the clinical application type indicates the non-lesion application;

apply the second region of interest to the B-mode ultrasonic image;

extract image features corresponding to the second region of interest in the B-mode ultrasonic image; and simultaneously output, to a display, the elasticity-related data corresponding to the first region of interest and the extracted image features corresponding to the second region of interest, wherein the elasticity-related data and the extracted image features comprise anatomical information of the overlapping portion.

12. The system of claim 11, wherein, when the selection of the clinical application type indicates the lesion application, the contour is generated by identifying contour points in the first region of interest and in a predefined area around the first region of interest.

13. The system of claim 11, wherein the image processing unit is further configured for:

using the first region of interest as the second region of interest.

14. The system of claim 11, wherein the user interface is configured for receiving a third input from the user to adjust the second region of interest and adjusting an outline of the second region of interest from a first outline to a second outline according to the third input received from the user, wherein the extracted image features correspond to image features within the second outline of the second region of interest in the B-mode ultrasonic image.

15. The system of claim 11, wherein the image features comprise a morphological feature, a texture feature, or a margin feature.

16. The system of claim 11, wherein the first region of interest is expanded to the second region of interest based on a segmentation technique.

17. The system of claim 11, wherein the image processing unit is configured to automatically generate the second region of interest without receiving a user input to set a boundary of the second region of interest.

18. The system of claim 11, further comprising a computer decision support system (CDS) in communication with the image processing unit and the elasticity measuring unit, wherein the CDS is configured to receive the image features corresponding to the second region of interest extracted from the B-mode ultrasonic image and the elasticity-related data corresponding to the first region of interest generated by the elasticity measuring unit to determine a diagnosis of anatomical features within the overlapping portion.

19. The system of claim 11, wherein the elasticity measuring unit is configured to control the ultrasonic probe to generate the elasticity-related data and the image processing unit is configured to automatically generate the second region of interest in parallel.

* * * * *